United States Patent [19]

Sugimori et al.

[11] Patent Number: 4,659,500

[45] Date of Patent: Apr. 21, 1987

[54] ESTER DERIVATIVE HAVING A POSITIVE DIELECTRIC ANISOTROPY

[75] Inventors: Shigeru Sugimori, Fujisawa; Kazunori Nigorikawa; Yasuyuki Goto, both of Yokohama, all of Japan

[73] Assignee: Chisso Corporation, Osaka, Japan

[21] Appl. No.: 774,945

[22] Filed: Sep. 11, 1985

[30] Foreign Application Priority Data

Sep. 11, 1984 [JP] Japan .................. 59-190378

[51] Int. Cl.[4] ............. C09K 19/54; C09K 19/34; G02F 1/13; C07D 213/79
[52] U.S. Cl. ............... 252/299.5; 252/299.61; 350/350 R; 546/326
[58] Field of Search ............. 252/299.5, 299.61; 350/350 R; 546/326

[56] References Cited

U.S. PATENT DOCUMENTS

| | | | |
|---|---|---|---|
| 4,198,312 | 4/1980 | Sato et al. | 252/299.67 |
| 4,455,261 | 6/1984 | Sasaki et al. | 252/299.67 |
| 4,490,276 | 12/1984 | Hsu | 252/299.61 |

FOREIGN PATENT DOCUMENTS

| | | | |
|---|---|---|---|
| 3315295 | 10/1984 | Fed. Rep. of Germany | 252/299.61 |
| 3510735 | 10/1985 | Fed. Rep. of Germany | 252/299.61 |
| 60-149564 | 8/1985 | Japan | 252/299.61 |
| 60-163865 | 8/1985 | Japan | 252/299.61 |
| 2161808 | 1/1986 | United Kingdom | 252/299.61 |
| 1069413 | 4/1985 | U.S.S.R. | 252/299.61 |
| 1063101 | 6/1985 | U.S.S.R. | 252/299.61 |

OTHER PUBLICATIONS

Pavluchenko, A. I., et al., J. De Physique, Coll C3, Suppl. No. 4, vol. 40, Apr. 1979, pp. C3-1-4.
Dewar, M. J. S., et al., Liquid Crystals and Ordered Fluids, vol. 2, Ed. Johnson, J., et al, Plenum Press, N.Y., pp 733-741 (1980).
Grachev, U. T., et al., Mol. Cryst. Liq. Cryst., vol. 65, pp. 133-144 (1981).

*Primary Examiner*—Teddy S. Gron
*Attorney, Agent, or Firm*—Fay, Sharpe, Beall, Fagan, Minnich & McKee

[57] ABSTRACT

A novel ester derivative affording a positive large dielectric anisotropy value ($\Delta\epsilon$) of liquid crystal compositions and also reducing the optical anisotropy value ($\Delta n$) thereof when the derivative is contained therein, and a liquid crystal composition containing the ester derivative are provided, which ester derivative is expressed by the formula

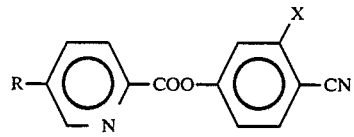

wherein R represents an alkyl group or an alkoxy group each of 1 to 10 carbon atoms and X represents F or Cl.

4 Claims, No Drawings

ESTER DERIVATIVE HAVING A POSITIVE DIELECTRIC ANISOTROPY

BACKGROUND OF THE INVENTION

This invention relates to a novel ester derivative useful as a component of liquid crystal compositions and a liquid crystal composition containing the same.

Display elements utilizing the optical anisotropy and dielectric anisotropy of liquid crystal substances have come to be broadly used. Depending on the kinds of liquid crystal display elements, physical properties required for liquid crystal substances used therein vary. For example, a positive dielectric anisotropy is required in some case or a negative dielectric anisotropy is required in another case. Further, liquid crystal substances are required to be stable to heat, air, light, moisture, etc. and also to exhibit liquid crystal phases in a temperature range as broad as possible. No single compound meeting such requirements has yet been found; hence liquid crystal compositions consisting of several kinds of liquid crystal compounds and if necessary, non-liquid crystal compounds have been practically used.

For display elements of twist-nematic mode which have currently been most often used, there have been desired liquid crystal substances having a positive large dielectric anisotropy value (hereinafter abbreviated to $\Delta\epsilon$) for reducing the threshold value of their driving voltage and also a small optical anisotropy value (hereinafter abbreviated to $\Delta n$) for reducing the visual angle-dependency of display elements.

A first object of the present invention is to provide a substance affording a positive large $\Delta\epsilon$ of liquid crystal compositions and also reducing the $\Delta n$ thereof when the substance is contained therein.

A second object of the present invention is to provide a liquid crystal composition containing such a substance.

SUMMARY OF THE INVENTION

The present invention resides in an ester derivative expressed by the formula

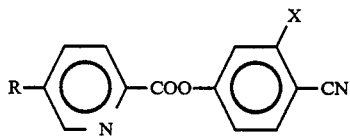

(I)

wherein R represents an alkyl group or an alkoxy group each of 1 to 10 carbon atoms and X represents F or Cl, and a liquid crystal composition containing the ester derivative of the formula (I).

DETAILED DESCRIPTION OF THE PREFERRED EMBODIMENTS

Concrete examples of the compound of the formula (I) are as follows:
3-fluoro-4-cyanophenyl 5-methylpicolinate,
3-fluoro-4-cyanophenyl 5-ethylpicolinate,
3-fluoro-4-cyanophenyl 5-n-propylpicolinate,
3-fluoro-4-cyanophenyl 5-n-butylpicolinate,
3-fluoro-4-cyanophenyl 5-n-pentylpicolinate,
3-fluoro-4-cyanophenyl 5-n-hexylpicolinate,
3-fluoro-4cyanophenyl 5-n-heptylpicolinate,
3-fluoro-4-cyanophenyl 5-n-octylpicolinate,
3-fluoro-4-cyanophenyl 5-n-nonylpicolinate,
3-fluoro-4-cyanophenyl 5-n-decylpicolinate,
3-fluoro-4-cyanophenyl 5-methoxypicolinate,
3-fluoro-4-cyanophenyl 5-ethoxypicolinate,
3-fluoro-4-cyanophenyl 5-n-propoxypicolinate,
3-fluoro-4-cyanophenyl 5-n-butoxypicolinate,
3-fluoro-4-cyanophenyl 5-n-pentoxypicolinate,
3-fluoro-4-cyanophenyl 5-n-hexyloxypicolinate,
3-fluoro-4-cyanophenyl 5-n-heptyloxypicolinate,
3-fluoro-4-cyanophenyl 5-n-octyloxypicolinate,
3-fluoro-4-cyanophenyl 5-n-nonyloxypicolinate,
3-fluoro-4-cyanophenyl 5-n-decyloxypicolinate,
3-chloro-4-cyanophenyl-5-methylpicolinate,
3-chloro-4-cyanophenyl 5-ethylpicolinate,
3chloro-4-cyanophenyl 5-n-propylpicolinate,
3-chloro-4-cyanophenyl 5-n-butylpicolinate,
3-chloro-4-cyanophenyl 5-n-pentylpicolinate,
3-chloro-4-cyanophenyl 5-n-hexylpicolinate,
3-chloro-4-cyanophenyl 5-n-heptylpicolinate,
3-chloro-4-cyanophenyl 5-n-octylpicolinate,
3-chloro-4-cyanophenyl 5-n-nonylpicolinate,
3-chloro-4-cyanophenyl 5-n-decylpicolinate,
3-chloro-4-cyanophenyl 5-methoxypicolinate,
3-chloro-4-cyanophenyl 5-ethoxypicolinate,
3-chloro-4-cyanophenyl 5-n-propoxypicolinate,
3-chloro-4-cyanophenyl 5-n-butoxypicolinate,
3-chloro-4-cyanophenyl 5-n-pentoxypicolinate,
3-chloro-4cyanophenyl 5-n-hexyloxypicolinate,
3-chloro-4-cyanophenyl 5-n-heptyloxypicolinate,
3-chloro-4-cyanophenyl 5-n-octyloxypicolinate,
3-chloro-4-cyanophenyl 5-n-nonyloxypicolinate, The compound of the present invention expressed by the formula (I) may be prepared by condensing a 5-substituted picolinic acid (IV) with a 3-halogeno-4-cyanophenol (V) in methylene chloride solvent using dicyclohexylcarbodiimide. This reaction is shown by the following equation:

wherein R and X are as defined above.

Examples of components other than the compound of the present invention, usable as components of the liquid crystal composition of the present invention are liquid crystal compounds of esters, Schiff's bases, biphenyls, phenylcyclohexanes, heterocyclic compounds, etc. Examples of liquid crystal compounds of esters are trans-4-alkylcyclohexanecarboxylic acid-4-alkylphenyl esters, trans-4-alkylcyclohexanecarboxylic acid-4-alkoxyphenyl esters, 4-alkoxybenzoic acid-4-alkylphenyl esters, 4-alkylbenzoic acid-4-cyanophenyl esters, 4-(trans-4-alkylcyclohexyl) benzoic acid-4-cyanophenyl esters, etc. Examples of liquid crystal compounds of Schiff's bases are 4-alkoxybenzylidene-4-alkanoyloxyanilines, 4-alkoxybenzylidene-4-alkylanilines, 4-alkoxybenzylidene-4-cyanoanilines, etc. Examples of liquid crystal compounds of biphenyls are 4'-alkyl-4-cyanobiphenyls, 4'-alkoxy-4-cyanobiphenyls, cyanobiphenyls, 4'-alkoxy-4-alkylbiphenyls, etc. Examples of liquid crystal compounds of phenylcyclohexanes are trans-4-alkyl-(4-cyanophenyl) cyclohexanes, trans-4-alkyl-(4-alkoxyphenyl) cyclohexanes, etc. Examples of liquid crystal compounds of heterocyclic compounds are 5-alkyl-2-(4-cyanophenyl)-1,3-dioxanes, 5-alkyl-2-(4-cyanophenyl) pyrimidines, 5-cyano-2-(4-alkylphenyl) pyrimidines, etc.

The content of the compound of the present invention in the composition of the present invention varies depending on the kinds of other components to be mixed therewith, but it is usually 1 to 30% by weight, preferably 5 to 15% by weight based on other components. A concrete example is 30 to 1% by weight of the ester derivative(s) of the present invention based on 70 to 99% by weight of a 4-alkyl-(4-cyanophenyl) cyclohexane, alone or a mixture of several kinds thereof, preferably 15 to 5% by weight of the former based on 85 to 95% by weight of the latter.

Another example is 1 to 30% by weight of the ester derivative(s) of the present invention based on 60 to 84% by weight of a trans-4-alkyl-(4-cyanophenyl) cyclohexane, alone or a mixture of several kinds thereof and 10 to 15% by weight of a 4-cyano-4'-(trans-4-alkylcyclohexyl)biphenyl, alone or a mixture of several kinds thereof, preferably a composition having a proportion of these three compounds of 5 to 15% by weight, 72 to 81% by weight, and 12 to 15% by weight, respectively.

Japanese patent application laid-open No. Sho 58-83665 (corresponding U.S. Pat. No. 4,455,261) discloses a compound expressed by the formula

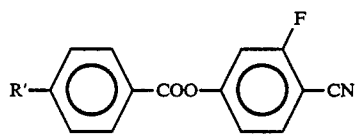

(VI)

wherein R' represents a linear chain alkyl group of 1 to 10 carbon atoms, and also discloses that when a representative example of the compound of the forumula (VI) wherein R' represents n-propyl group is added to other liquid crystal mixtures, it is possible to reduce the threshold value of driving voltage.

The ester derivative of the present invention expressed by the formula (I) exhibits by itself no liquid crystal, phase, but it has a good compatibility with other liquid crystals or liquid crystal mixtures, and its addition results in an effectiveness of moving the dielectric anisotropy value ($\Delta\epsilon$) of the resulting liquid crystal compositions toward the positive side to a large extent and also reducing their optical anisotropy value ($\Delta n$). For example, a representative example of the compound of the formula (I) wherein R represents n-butyl group can make the dielectric anisotropy value larger, make the threshold value of driving voltage lower and make the optical anisotropy value less, in the same quantity added, than those of a representative example of the compound of the formula (VI) wherein R' represents n-propyl group. These facts will be evidenced by the following Examples and Comparative examples.

EXAMPLE 1

Preparation of 3-fluoro-4-cyanophenyl 5-n-butylpicolinate 5-n-butyl picolinic acid (1.8 g) and 3-fluoro-4-cyanophenol (1.4 g) were dissolved in methylene chloride (30 ml). While the resulting solution was kept at 0° C. or lower, a solution (20 ml) of dicyclohexylcarbodimide (2.1 g) in methylene chloride was dropped to the above solution, followed by further agitating for 3 hours, filtering off the resulting solids, adding 2N-NaOH aqueous solution to the filtrate, separating the methylene chloride layer, washing it with water till the washing water became neutral, distilling off the solvent from the methylene chloride layer and recrystallizing the residue from ethanol to obtain the objective 3-fluoro-4cyanophenyl 5-n-butylpicolinate (0.3 g) having a m.p. of 45.1°–46.1° C.

EXAMPLE 2

A liquid crystal composition (A) consisting of trans-4-propyl-(4-cyanophenyl) cyclohexane 24% by weight, trans-4-pentyl-(4-cyanophenyl) cyclohexane 36% by weight, trans-4-heptyl-(4-cyanophenyl) cyclohexane 25% by weight and 4-cyano-4'-(trans-4-pentylcyclohexyl) biphenyl 15% by weight, has a nematic-clearing point of 72.0° C., $\Delta\epsilon$ of +11.6 and $\Delta n$ of 0.140. This composition (A) was sealed in a TN cell (cell thickness: 10 μm) having opposed transparent electrodes. The resulting liquid crystal cell exhibited a threshold voltage of 1.75 V and a saturation voltage of 2.40 V at 20° C.

A liquid crystal composition (B) consisting of the above liquid crystal composition (A) (85% by weight) and 3-fluoro-4-cyanophenyl 5-n-butylpicolinate (15% by weight) prepared in Example 1 had a nematic-clearing point of 58.4° C., $\Delta\epsilon$ of +16.5 and $\Delta n$ of 0.133. This composition (B) was filled in the same TN cell as the above. The resulting liquid crystal cell exhibited a threshold voltage of 1.29V and a saturation voltage of 1.69V, at 20° C.

COMPARATIVE EXAMPLE 1

A liquid crystal composition (C) consisting of the above liquid crystal composition (A) (85% by weight) and 3-fluoro-4-cyanophenyl n-propylbenzoate (15% by weight) had a nematic-clearing point of 63.8° C., $\Delta\epsilon$ of 16.3 and $\Delta n$ of 0.139. This composition (C) was filled in the same TN cell as above. The resulting liquid crystal cell exhibited a threshold voltage of 1.33 V and a saturation voltage of 1.86 V, at 20° C.

What we claim is:

1. An ester derivative expresed by the formula

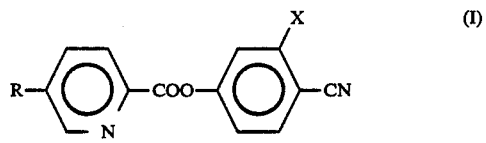

(I)

wherein R represents an alkyl group or an alkoxy group each having 1 to 10 carbon atoms and X represents F or Cl.

2. An ester derivative according to claim 1, expressed by the formula

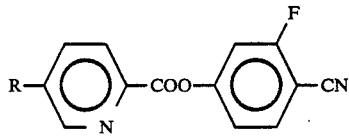 (II)

wherein R represents an alkyl group or an alkoxy group each having 1 to 10 carbon atoms.

3. An ester derivative according to claim 1 expressed by the formula

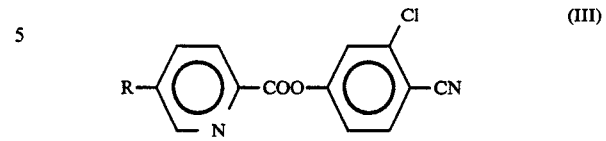 (III)

wherein R represents an alkyl group or an alkoxy group each having 1 to 10 carbon atoms.

4. A liquid crystal composition having at least two components at least one of which is a compound as set forth in claim 1.

* * * * *